United States Patent [19]

Klein et al.

[11] Patent Number: 4,659,473

[45] Date of Patent: Apr. 21, 1987

[54] PROCESS FOR MAINTAINING A CHARGE OF A MICROPOROUS MOLDED ARTICLE

[75] Inventors: Wolfgang Klein, Klingenberg; Klaus Schneider, Erlenbach, both of Fed. Rep. of Germany

[73] Assignee: Akzo NV, Arnhem, Netherlands

[21] Appl. No.: 708,398

[22] Filed: Mar. 5, 1985

[30] Foreign Application Priority Data

Mar. 8, 1984 [DE] Fed. Rep. of Germany ....... 3408511
May 21, 1984 [DE] Fed. Rep. of Germany ....... 3418870

[51] Int. Cl.$^4$ ............................................. B01D 13/01
[52] U.S. Cl. ................................... 210/638; 210/643; 210/644
[58] Field of Search ............... 210/638, 643, 644, 651; 55/16

[56] References Cited

U.S. PATENT DOCUMENTS

| | | | |
|---|---|---|---|
| 3,228,877 | 1/1966 | Mahon | 210/321.3 X |
| 3,566,580 | 3/1971 | Li | 55/16 |
| 3,970,219 | 7/1976 | Spitzer et al. | 222/402.24 X |
| 4,239,506 | 12/1980 | Steigelmann et al. | 210/651 |
| 4,247,498 | 1/1981 | Castro. | |
| 4,437,994 | 3/1984 | Baker | 210/651 X |
| 4,564,373 | 1/1986 | Schmitz et al. | 210/638 X |

FOREIGN PATENT DOCUMENTS 2910793 2/1980 Fed. Rep. of Germany.
3107874 9/1982 Fed. Rep. of Germany.

*Primary Examiner*—David Sadowski
*Attorney, Agent, or Firm*—Parkhurst & Oliff

[57] ABSTRACT

A process for maintaining a charging medium in a microporous molded article for carrying out material transfer processes is described. A charging medium is supplied or presented to the molded article while the material transfer processes are being carried out. This supply takes place on a part of the surface of the molded article which does not participate in the material transfer process. The molded articles are preferably membranes. The process compensates for a loss of medium in the pores of the molded article without requiring the material transfer process to be interrupted.

An apparatus suitable for carrying out the process is also described.

The process may advantageously be used inter alia for controlled release or slow release processes and processes for facilitated or coupled transport of metal ions.

20 Claims, 1 Drawing Figure

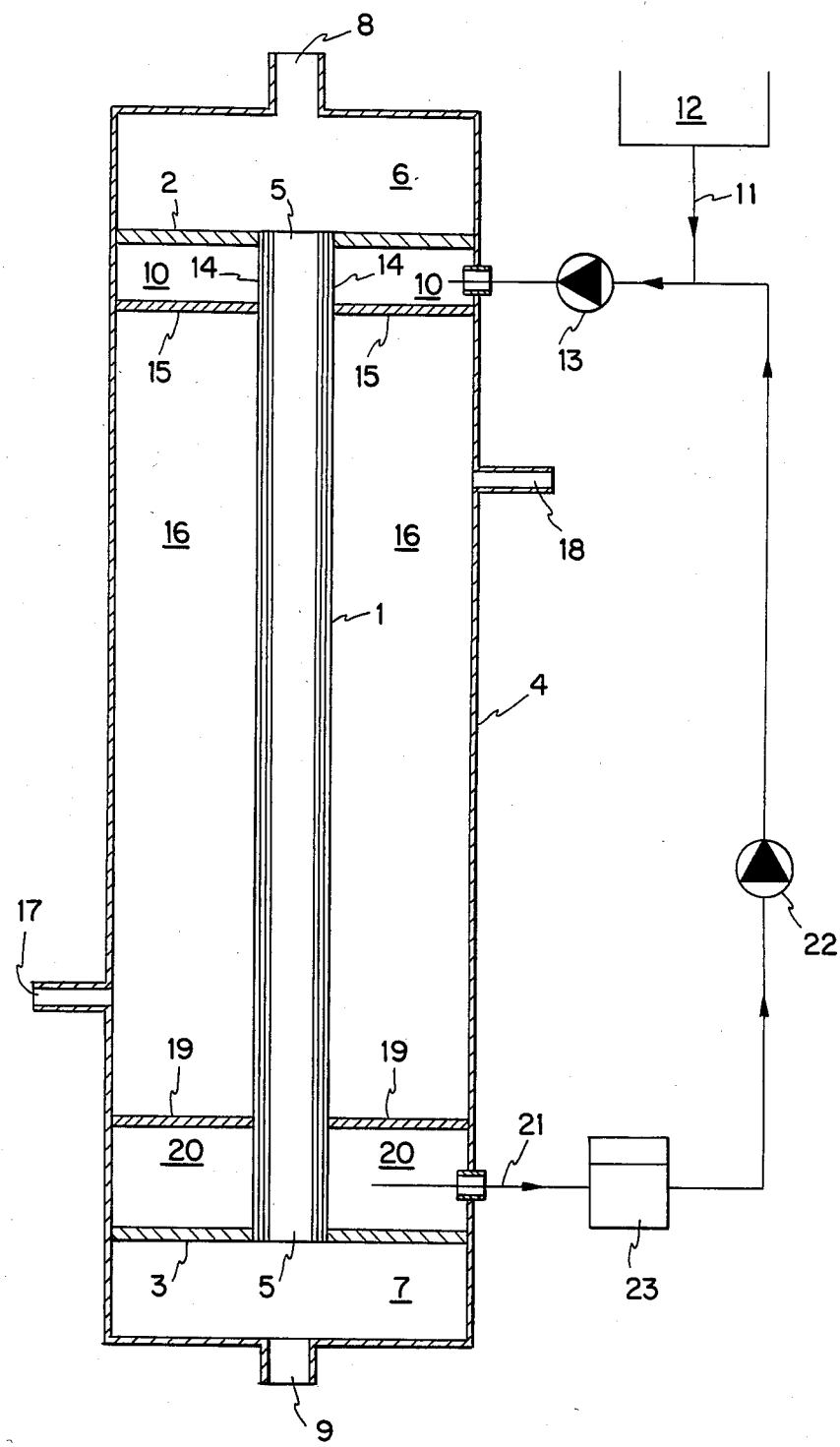

PROCESS FOR MAINTAINING A CHARGE OF A MICROPOROUS MOLDED ARTICLE

This invention relates to a process and apparatus for maintaining a charge in microporous molded articles for carrying out material transfer processes.

BACKGROUND OF THE INVENTION

Material transfer processes using porous molded articles are known and are widely used in medicine, industry and agriculture. Examples include slow release or controlled release processes in which an active substance, contained in the pores of a carrier substance, is required to be slowly released to the surroundings. Other examples include transport processes such as the facilitated or coupled transport of metal ions through the walls of porous membranes, as described inter alia in German Offenlegungsschrift No. 2,910,793. In these and similar processes, the membrane pores contain a complex-forming agent so that the metal ions are transported by way of their complexes.

One disadvantage of the processes mentioned above is loss of the medium with which the pores of the molded article or membrane are charged. In controlled release processes, the loss is due to the release of active substance to the surroundings and necessitates regeneration of the molded article at certain time intervals. One possible result of this loss is that the rate of release may slow down to an undesirable extent after some time, for example when a considerable proportion of the active substance has already been released. In processes for the transport of substances such as metal ions through the pores of a membrane, in which the transport is mediated or facilitated by the medium in the pores, a considerable proportion of this medium is liable to be loss after prolonged operation of the process. This initially results in a reduction of the flow rate in the process, i.e., a reduction in the quantity of metal ions transported per unit time. The process must finally be stopped or comes to a standstill of its own accord.

These known processes have the disadvantage that the charge of the porous molded articles cannot be maintained during the transfer of material. Recharging of the porous article can only take place when the transfer of material has been stopped or interrupted. Recharging is therefore not only in many cases a cumbersome process but also invariably increases the cost of the material transfer process.

SUMMARY OF THE INVENTION

It was therefore an object of the present invention to provide a process in which the charge in microporous molded articles could be maintained during the material transfer process without this process having to be interrupted, so that expensive operations of cleaning and intermittently recharging the molded article could be avoided and the continued maintenance of the charge would enable the material transfer processes to be carried out continuously over very long periods without any loss in efficiency. It was another object of the invention to provide an aparatus for carrying out the process.

According to the invention, the solution to the problem lies in choosing a material for the molded article which has a pore system extending throughout its structure and maintaining the charge of the molded article while the material transfer processes are being carried out by supplying a charging medium to that surface of the molded article which does not participate in the material transfer process.

This ensures, as will be explained below, that the charging medium or parts thereof can penetrate into the pore system of the molded article during the material transfer process when parts of the medium with which the molded particle has already been charged depart from the surfaces of the molded article.

BRIEF DESCRIPTION OF THE DRAWING

The drawing shows a schematic representation of the method and apparatus of the invention.

DETAILED DESCRIPTION OF THE INVENTION

A charging medium is supplied to a portion of the surface of a microporous molded article which does not take part in the material transfer. It is therefore necessary for the process according to the invention not to use the whole surface of the microporous molded article for the material transfer but to reserve a part of the surface which does not participate in this transfer. This part of the surface need not be large, a proportion far below 50% of the total surface area being generally sufficient, so that most of the surface of the molded article may be used for the material transfer.

The process according to the invention may be employed during the operation of material transfer processes in which microporous molded articles containing a medium in their pores are used. Examples of such material transfer processes are the transport or material release processes. In transport processes, for example, one or more constituents are separated from a system situated on one of the surfaces of the molded article. The molded articles in such cases are generally membranes. The constituents which are to be separated selectively are transported through the membrane to the other surface, and the medium present in the pores may ensure the selectivity of the process and it may facilitate transport, e.g. by complex formation with metal ions. One example of release processes is the controlled or slow release process in which the medium in the pores is released to the surroundings.

In order that these material transfer processes may be able to continue for a long time, the process according to the invention provides for the maintenance of a charge in the molded articles. This means that the pores of the molded article are kept at least partly filled or charged with the charging medium. In individual cases, the entire pore volume need not necessarily be kept filled with a medium but only at least a sufficient proportion of the total volume to ensure that the material transfer process may continue for a long time without loss of efficiency. In particular, the supply of a charging medium during the material transfer process ensures that any loss of medium with which the pores are charged, i.e. partly or completely filled, can be compensated by the charging medium.

By "supply of a charging medium" is meant in the context of this invention that the charging medium is presented to the molded article at a part of the surface of the latter not participating in the material transfer while the material transfer process is taking place. In some cases, the charing medium need not be continuously applied to the charging surface. Instead, intermittent supply of a gas or, in the case of a liquid charging medium, intermittent supply by dripping or the like, may be sufficient.

In a preferred embodiment of the process, however, the charging medium is supplied continuously. According to another preferred embodiment, a layer of charging medium is constantly maintained on that surface of the molded article which is provided for the supply of charging medium, e.g. by keeping this surface in constant contact with a reservoir of gaseous or liquid charging medium.

The presentation of charging medium enables this medium to penetrate into the pore system of the molded article when the state of charging of the artilce requires this, i.e. when medium with which the pores are charged leaves the surface of the molded article.

If the charging medium is gaseous, this penetration into the pore system may be assisted by exerting a pressure on the gas on the surface provided for supplying the medium. For reasons of cost, it may be advantageous to employ the static pressure of the gas itself, e.g. by arranging a reservoir of gas at a higher level than the aforesaid surface, the reservoir being designed to supply gas to this surface. According to a preferred embodiment of the process, therefore, pressure is exerted on the layer of the charging medium, and according to another preferred embodiment, the pressure is a static pressure produced by the charging medium itself. This also applies to the case where the charging medium is a liquid.

In a preferred embodiment, the charging medium has the same components as the medium with which the pore system is already charged, that is to say, it has the same qualitative composition. In some cases, however, the qualitative compositions may differ, e.g. if the charging medium is required to supply a component not yet present in the pore system, in order to bring about a deliberate change i the conditions of the material transfer process.

According to a preferred embodiment, both the charging medium and the medium already present in the pores are liquid. As already mentioned, dripping liquid onto a part of the surface of the molded article may be used. The following method may also be employed for the process according to the invention: Part of the surface of the molded article not participating in the material transfer is in contact with a layer of liquid charging medium which in turn communicates with a larger quantity of this liquid, e.g. a reservoir of this liquid. When required by the state of charging of the pore system, the liquid can enter the pore system from the aforesaid layer on the surface and fresh liquid can be supplied to this surface layer from the reservoir. The entry of liquid charging medium into the pore system of the molded article may be enabled or facilitated by various means, as follows:

a. In the simplest case, the porous molded article is placed vertically and the surface of contact between the molded article and the liquid in the reservoir is situated at the upper end of the article. In this case, the hydrostatic pressure effects or assists the flow of replacement liquid.

b. An excess pressure may be applied to the liquid in the reservoir and/or to the liquid layer on the surface of the molded article provided for this layer.

c. If the liquid used for the charging medium is one which easily wets the material of the molded article, then the liquid is sucked into the article by capillary forces as soon as a portion of the medium in the pores leaves the pore system. If the charging medium is required to contain a component which does not so readily wet the material of the molded article, wetting can be improved by the addition of an easily wetting solvent.

d. In a preferred embodiment, the flow of replacement liquid from the surface layer into the pore system may be effected or assisted by applying a vacuum to the pore system on a portion of the surface of the molded article which does not take part in the material transfer. Such a vacuum may be applied continuously or intermittently. The vacuum causes small quantitites of liquid to be withdrawn from the pores, but these quantities of liquid may be collected and returned to the charging medium in the reservoir. This assistance of the flow by application of a vacuum results in a more rapid flow and hence more rapid replacement of any liquid loss in the pores. The withdrawal of medium from the pores, for example by application of a vacuum, also has the advantage that a medium in the pores may be replaced by another medium if required, e.g. if the conditions of material transfer are to be altered. According to a preferred embodiment of the process, therefore, medium contained in the microporous molded article is also withdrawn during the material transfer process and optionally transferred to the charging medium.

The portion of molded article surface where the charging medium is supplied may be situated on any part of the molded article, but is preferably arranged at one end of the molded article so that the charging medium used for refilling flows in one direction only.

It may be advantageous, especially when the molded article is very large, to supply charging medium to a portion of the surface at each end so that any loss of medium in the pores or parts thereof can be compensated more rapidly. In that case, liquid layers may be provided at both the aforesaid parts of the surface and fed with charging medium from a common reservoir, and a certain excess pressure may be employed for more rapid refilling. In such an arrangement, a zone on the surface of the molded article situated approximately halfway between the two above mentioned portions of surface may be separated from the material transfer surface by separating elements. This zone may then be connected to a receiving device for liquid so that small quantities of liquid lost from the pore system due to excess pressure may be recovered and returned to the reservoir. This receiving device may include a source of vacuum.

As already mentioned, the porous molded article may be arranged vertically so that the flow of charging medium may be effected or assisted by hydrostatic pressure. In controlled release processes, however, a horizontal arrangement may sometimes be preferable so that the charging medium will not exert any pressure on the medium in the pores and the medium or parts thereof can therefore be released very slowly to the surroundings. In that case, the replacement of liquid can be effected by capillary action alone. A precondition for this is that the charging medium, with or without a solvent, should efficiently wet the material of the molded article.

The molded articles used in the process according to the invention are microporous. For the purpose of this invention, this means that no pores in the molded article have an average diameter greater than about 10 $\mu$m. The term "microporous" for the purpose of this invention also includes molded articles which do not have pores in the true sense of the word, as for example molded articles which have a structure of the kind used for ultrafiltration or dialysis membranes. Such molded articles, which have no apertures or pores greater than about 800 to 1000 Å in diameter, are suitable for the process according to the invention since they are used for material transfer processes. The choice of a microporous molded article for the process according to the invention must be adjusted in individual cases to the nature of the charging medium since this must be able to penetrate into the structure of the molded article. If the charging medium is gaseous, microporous molded articles which have no openings or pores with a diameter greater than about 1000 Å are particularly suitable. If the charging medium is liquid, as in a preferred embodiment, then the molded article is generally required to have definite pores. The average diameter of the pores is in this case from about 0.05 to about 10 μm. This ensures that the liquid charging medium is able to penetrate into the pore system.

According to a preferred embodiment of the process, the molded articles used have a pore structure which includes cells as well as pores. Such molded articles are very suitable for material transfer processes. The approximately spherical cells of these articles generally have an average diameter of about 0.5 to about 100 μm, preferably from 1 to 20 μm. Such a molded article is capable of storing a larger quantity of medium than one which has a smaller pore volume. An increase in the quantity of medium in the pore system is desirable since it reduces the risk of medium being lost more rapidly than it can be replaced by the charging medium, e.g. by capillary forces. Connecting ducts, the pores, are present between the cells. These ducts constitute the narrowest zones for the transport of material and ensure, for example, that no impurities in the form of larger particles can pass through the wall of the molded article from one of its surfaces to the other during the material transfer processes. These pores have an average diameter which is smaller by a factor of 2 to 200, preferably a factor of 5 to 40 than the diameter of the spherical cells. The average pore diameter is preferably in the region of about 0.05 to about 10 μm.

The molded articles used must have a continuous pore system extending throughout their structure so as to enable the charging medium entering at the surface of the molded article to penetrate the whole pore system. This means that charging medium must be able to flow into substantially the whole pore system through the pores or connecting ducts. The presence of a few pores which have no communication with the whole pore system may in some cases have no deleterious effect, e.g., in controlled release processes. Although these isolated pores are not available for the process according to the invention, they are so small in number that their contribution to the release of active substance is insignificant so that no harm is done if the substance contained in them cannot be replaced. It is necessary, however, that the predominant proportion of the pores, preferably all the pores, should communicate with each other and with the charging medium present for replacement on the surface of the molded article.

In a preferred embodiment of the process, the microporous molded articles are membranes in the form of flat films, tubes, pipes or hollow fibers of the kind used for material transfer processes and separating processes.

Suitable microporous membranes having a continuous pore structure with a pore system consisting of cells and connecting ducts, the pores proper, have been described inter alia in U.S. Pat. No. 4,247,498. The relevant passages of the said document are hereby incorporated by reference. The membranes used preferably have a high porosity, i.e., a high ratio of volume formed by the pores and cells to the the total volume of the membrane. High pore volumes of from 70 to 80% are particularly suitable for material transfer processes since the greater quantity of medium present in the pores leads to greater efficiency. In processes of facilitated or coupled transport of metal ions, for example, a high pore volume enables a larger quantity of complex former to be accommodated in the pores, whereby the quantity of metal ions transported per unit time by way of complex formation is increased. According to a preferred embodiment of the process, therefore, the molded articles used have a pore volume of 70 to 80%.

The wall thickness of microporous membranes which are particularly suitable for the process according to the invention may vary within wide limits. In a preferred embodiment, the wall thickness is in the range of from 100 to 300 μm.

Although the process according to the invention may equally be carried out with greater wall thicknesses, thick walls have the effect, for example in processes of facilitated or coupled transport of metal ions, of increasing the length of the path which the metal ions in complex form must travel through the membrane wall by diffusion. This has the effect of slowing down the process to an undesirable extent. With wall thicknesses of less than 100 μm, problems due to mechanical instability may occasionally arise, especially when an excess pressure or vacuum is applied. This may occur mainly when the membranes used have a large pore volume, which often amounts to 70 to 80% of the total volume.

If the process according to the invention is to be used for controlled release or slow release processes, the microporous molded articles need not be membranes. If, for example, a perfume is to be slowly released to the surrounding atmosphere over a prolonged period of time, the molded article may be in the form of a relatively thick microporous rod to which charging medium is supplied at one end over a portion of the surface which has no contact with the surroundings. In that case, it is necessary to provide for equalization of pressure in the charging medium. This may be achieved, for example, if a small portion of the surface of a reservoir containing the charging medium comprises a membrane which is permeable to air but not to the charging medium.

It is in many cases advantageous, and in some cases even essential, to use microporous molded articles or membranes in which the internal surface consists of a hydrophobic material.

This is necessary, for example, in processes of facilitated or coupled transport of metal ions taking place via complex formation, where a complex former is situated in the pores. In that case, the aqueous solutions which take up and release metal ions and which are situated on the membrane surfaces must be prevented from entering the pore system and displacing the complex former. This requirement may be fulfilled, for example, by using a uniform hydrophobic material in which water can enter the pores only at significantly higher pressures than non-polar organic liquid. In an alternative arrangement, only the internal surfaces of the molded article are hydrophobic, i.e., the surfaces of the pores and, where present, also the cells are hydrophobic. If molded articles made of a material which is not hydrophobic are to be used, then the internal surface can be rendered hydrophobic, e.g., by applying a hydrophobic coating by impregnation. The use of a molded article with a hydrophobic internal surface for the process according to the invention constitutes a preferred embodiment and provides for efficient wetting with a hydrophobic, non-polar liquid charging medium. Such a liquid readily enters the pore system and replacement of liquid from the surface of the molded article into the pore system can normally take place by capillary forces alone, as already mentioned above, without requiring a pressure differential. In a preferred embodiment of the process according to the invention, therefore, the charging medium used is a liquid which readily wets the material of the molded article. Efficient wetting exists when a drop of the liquid charging medium placed on a flat surface of the molded article spreads out easily, i.e. if it has a boundary angle of less than about 20°. Under ideal conditions of complete wetting, this angle is 0°.

In a preferred embodiment, the molded article comprises polypropylene.

Molded articles or membranes of microporous polypropylene, e.g. of Accurel$^R$ (Enka AG, Wuppertal), have proved to be particularly suitable for the process according to the invention. Other suitable materials include, e.g., other polyolefins and halogenated polyolefins.

As already mentioned above, the charging medium preferably has the same qualitative composition as the medium with which the pores are already charged. If both media comprise a mixture of two or more components, then it is often advantageous if the charging medium has a different quantitative composition from that of the medium in the pores since it may occur that one component of the medium in the pores leaves the pore system more readily than another. In that case, the component which leaves more readily must be replaced at a higher rate by the charging medium. One example of such a case is the already mentioned facilitated or coupled transport of metal ions. In this case, the medium frequently consists of a non-polar solvent in which a complex former is dissolved. Since complex formers have polar properties to a certain extent, the complex formers used are liable to be slightly soluble in the aqueous solutions on the membrane surfaces, and this solubility may result in a gradual reduction in the quantity of complex formers in the pores while the quantity of non-polar solvent in the pores is maintained. In that case, the complex former must be replaced by fresh complex former from the charging medium, mainly by diffusion. In order to increase the rate of this diffusion, it is advisable to adjust the concentration of complex former in the charging medium to a higher level than the concentration of complex former in the medium present in the pores.

In a preferred embodiment of the process, therefore, the charging medium is a mixture of two or more components, in which at least one component is present at a higher concentration in the charging medium than in the medium with which the pores are already charged. In addition, in the case where predominantly one component is required to be replaced, e.g. by diffusion, it is also advantageous to apply a slight vacuum to the pore system, either intermittently or continuously. For this purpose, it is advantageous if the surface of contact between the charging medium and the molded article is situated at one end of the molded article while the point where a vacuum is applied is situated at the opposite end. This arrangement provides for a more rapid replacement flow of the more readily lost component.

The process according to the invention may be employed for all processes in which microporous molded articles of the type described above are used and in which portions of the medium present in the pores are liable to leave the pores during the process. For this purpose, the molded articles must be so constructed and designed that charging medium can be supplied to a portion of their surface which does not take part in the material transfer. In particular, in a preferred embodiment of the process, the invention is used for transport processes. One such process for which the process according to the invention is very suitable is the facilitated or coupled transport of metal ions. In this process, microporous membranes having a hydrophobic internal surface are used, in which the pores contain at least one complex former which is at most only slightly soluble in water. The aqueous solution releasing metal ions is situated on one of the membrane surfaces while the aqueous solution taking up metal ions is situated on the other membrane surface. The two aqueous solutions have a pressure which is lower than the minimum pressure required (the so-called liquid entry pressure) to enable them to enter the pores. If complex former leaves the pores during the process, for example due to a certain solubility in water, then it is replaced by the charging medium. It is thereby possible to achieve much longer operating times of the membrane than in known processes, which must be stopped as soon as the loss of complex former exceeds a certain value.

One particularly preferred apparatus for carrying out the process according to the invention contains a bundle of parallel microporous hollow fibers which are fixed in a housing by means such as an embedding compound. The apparatus is shown schematically in simplified, longitudinal section in the Figure where the sake of clarity only one hollow fiber is shown.

The Figure shows a hollow fiber 1 built into a housing 4 by means of embedding compound 2 and 3. The lumen of the hollow fiber 5 communicates with chamber 6 and chamber 7 at the upper and lower ends, respectively, of the hollow fiber. The chambers 6 and 7 have liquid inlet and outlet 8 and 9, respectively.

Adjacent to the embedding compound 2 is a chamber 10 which is separated from the chamber 6 by the embedding compound 2 so that no liquid exchange and, if necessary, no gas exchange can take place between them. Chamber 10 contains a charging medium. A pipe 11 leading into the chamber 10 communicates with a larger container 12 for charging medium. Situated between the container 12 and chamber 10 is a pump 13 with which an excess pressure can be produced in the charging medium in the chamber 10. Elements 11, 12 and 13 are not absolutely necessary for carrying out the process according to the invention. The presence of a liquid filled chamber 10 may be sufficient, depending on the particular process to be carried out and the dimensions of the apparatus. If elements 11, 12 and 13 are omitted, chamber 10 is closed to the outside by the housing 4, and all that is necessary is to ensure equalization of pressure in the chamber so that liquid can flow into the pore system for replacement.

The charging medium in chamber 10 is in contact with an outer side surface portion 14 of the surface of the hollow fiber. The chamber 10 is sealed off liquid-tightly or gas-tightly from the next chamber 16 by a separating element 15. This separating element 15 may be made of the same embedding compound, e.g. polyurethane, as the embedding compound 2 and 3. Chamber 16 is available for material transfer and contains an inlet and outlet (17 and 18) for liquid. Chamber 16 is separated liquid-tightly and, if necessary, gas-tightly from the adjacent chamber 20 by a separating element 19. This separating element 19 may again consist of the above-mentioned embedding compound. A pipe 21 for liquid leads to a pump 22 and from there into the pipe 11. Liquid can therefore be pumped from the container 10 into the chambers 10 and 20 by means of a pump 13 and/or 22 and an excess pressure can be built up in these chambers.

On the other hand, a receiver 23 for liquid may be provided to catch liquid entering the chamber 20 from the pore system. In that case, the pump 22 may be used for continuously or intermittently producing a vacuum in the chamber 20 to accelerate the flow of liquid from the chamber 10 into the pore system. Chamber 20 is sealed off liquid-tightly and, if necessary, gas-tightly from chamber 7 by the embedding compound 3. The chamber 7 communicates with the lumen 5 of the hollow fiber and contains liquid outlet 9.

The apparatus may also contain heating elements (not shown), e.g., a heating jacket on the external surface of the housing 4 or heating jackets surrounding the liquid or gas pipes.

A particularly suitable apparatus for carrying out the process contains a bundle of parallel microporous hollow fibers 1 built into a housing 4 by means of embedding compound 2 and 3, where the following elements are arranged in succession in the longitudinal direction on the external surface of the hollow fibers:

a. an inlet chamber with an intake unit and communicating with the lumina of the hollow fibers, b. a charging medium inlet chamber which may communicate with a liquid container, a pump being optionally provided between the chamber and the container, c. a material transfer chamber having an inlet and an outlet, d. a charging medium outlet chamber having an outlet duct which may communicate with the charging medium inlet chamber and may carry a pump, a receiver for catching liquid being optionally provided between the charging medium outlet chamber and the pump, and e. an outlet chamber with an outlet communicating with the lumina of the hollow fibers.

Of course, this structure could be modified in numerous ways by one of skill in the art without departing from the scope of the present invention. When the apparatus described above is used for facilitated or coupled transport of metal ions, the aqueous solution or dispersion releasing metal ions, for example, enters the chamber 16 through the opening 17, and the release of metal ions to the medium in the pores containing a complex former takes place on the outer surface of the hollow fiber. The metal ions diffuse through the wall of the hollow fiber in the form of their complexes and on the internal surface of the wall they are transferred to an aqueous liquid flowing through the lumen 5. The circulation of aqueous liquids is in this case an advantage. The liquid releasing the metal ions leaves the chamber 16 through the opening 18 while the liquid receiving the metal ions enters the chamber 6 through the opening 8, flows through the lumen 5 and leaves the chamber 7 at the opening 9. The inlet and outlet ducts 17 and 18, respectively, are preferably arranged at opposite ends of the chamber 16.

When the process according to the invention is used for slow release or controlled release processes in which active substances are released, e.g. to the surrounding atmosphere, it is advantageous to use a simpler apparatus. The microporous molded articles may in this case be in the form, for example, of rods, which are less expensive to manufacture than hollow fibers. The housing 4, the chambers 6 and 7 and optionally also the chamber 20 may then be omitted so that the only element on the molded article is the chamber 10, which may be in communication with a larger container through a pipe 11.

The invention will now be further described with the aid of an example, which, however, is intended merely to be exemplary and non-limiting as to the disclosed invention.

EXAMPLE

The apparatus used was a glass vessel having a neck at its top end. A hollow fiber open at both ends was introduced vertically into the glass vessel through the neck but without the lower end of the hollow fiber touching the bottom of the vessel. The hollow fiber was connected to the neck of the vessel by means of an embedding compound. This embedding compound was arranged at such a distance below the top edge of the neck that a container was formed, which was sealed off at the bottom by the embedding compound, on the inside by the hollow fiber and on the outside by the neck of the glass vessel. The container was open at the top. This container served as a liquid reservoir which could be filled with charging medium. The hollow fiber consisted of microporous polypropylene and had an internal diameter of 1.8 mm and an external diameter of 2.6 mm. The polypropylene had a continuous pore structure with cells and connecting pores.

The maximum diameter of the narrowest parts of the connecting channels (pores) was about 0.55 $\mu$m, measured by the bubble point method.

Several experiments were carried out. At the beginning of each experiment, the pore system of the hollow fiber was filled by impregnating it with a 9.5% by weight solution of 2-hydroxy-5-nonyl-acetophenone oxime in cyclohexane. The glass vessel was filled with an aqueous $CuSO_4$ solution to just below the embedding compound so that most of the hollow fiber projecting below the embedding compound was in contact with the salt solution on its external surface and in its lumen. The salt solution was continuously pumped upwards through the lumen at a rate of about 1 m/sec. and then returned to the vessel.

The first experiment, which served as a comparison experiment, was carried out with the reservoir empty, i.e. without the supply of a charging medium. Small pieces were cut off the lower end of the hollow fiber at certain time intervals and the amount of substituted oxime contained in them was determined by UV spectroscopy after extraction. It was found that the oxime content dropped approximately linearly from its initial value to about 50% of its initial value over a period of about 700 hours.

In subsequent experiments, the reservoir was filled with a 59% by weight solution of the oxime in cyclohexane. The procedure was the same as in the comparison experiment, and liquid from the reservoir could flow into the pore system exclusively by capillary forces, by diffusion and hydrostatic pressure. After the experiment had been continued for about 100 hours, an increase in oxime content at the lower end of the hollow fiber was found which was 10%. After 300 hours, the increase amounted to about 20%, and after 500 hours to about 50%. Virtually no further increase was recorded after this time and the content remained approximately constant.

These results were reproducible with only slight deviations in several experiments.

What is claimed is:

1. A process comprising maintaining a charge of a medium in a microporous molded article for carrying out a facilitated material transport process wherein said medium facilitates transport of said material through said medium, said molded article having a pore system extending throughout its structure, by supplying a charging medium only to a surface of the molded article which does not participate in the facilitated material transport process while the facilitated material transport process is being carried out.

2. Process according to claim 1, wherein the charging medium comprises the same components as the medium with which the pore system is already charged.

3. Process according to claim 1, wherein the charging medium is supplied continuously.

4. Process according to claim 1, wherein a layer of the charging medium is constantly maintained on said surface of the molded article which does not participate in the facilitated material transport process.

5. Process according to claim 4, wherein pressure is exerted on said layer.

6. Process according to claim 5, wherein said pressure is a static pressure produced by the charging medium.

7. Process according to claim 4, wherein a vacuum is applied to the pore system on a second, surface of the molded article which does not participate in the facilitated material transport process.

8. Process according to claim 1, wherein a vacuum is applied to the pore system on a second surface of the molded article which does not participate in the facilitated material transport process.

9. Process according to claim 1, wherein at least a portion of said medium in the microporous molded article is withdrawn during the facilitated material transport process and delivered to the charging medium.

10. Process according to claim 1, wherein the charging medium is a mixture of two or more components, at least one component being present at a higher concentration in the charging medium than in the medium in the microporous molded article.

11. Process according to claim 1, wherein the charging medium is a liquid.

12. Process according to claim 11, wherein the charging medium comprises a liquid which efficiently wets the material of the molded article.

13. Process according to claim 1, wherein the molded article comprises a hydrophobic internal surface.

14. Process according to claim 1, wherein the molded article comprises polypropylene.

15. Process according to claim 1, wherein the molded article comprises membranes in the form of flat films, tubes, pipes or hollow fibers.

16. Process according to claim 15, wherein the membranes have a wall thickness in the range of from 100 to 300 $\mu$m.

17. Process according to claim 1, wherein the pore system comprises cells and connecting ducts between the cells.

18. Process according to claim 1, wherein the microporous molded article has a porosity of from 70 to 80% of said molded article.

19. Process according to claim 1, wherein said facilitated material transport process is selected from the group consisting of facilitated transport of metal ions and coupled transport of metal ions.

20. A process comprising maintaining a charge of a medium in a hollow microporous molded article for carrying out a facilitated material transport process wherein said medium facilitates transport of said material through said medium, said molded article having a pore system extending throughout its structure, by supplying a charging medium to an outer side surface of the hollow molded article which does not participate in the facilitated material transport process while the facilitated material transport process is being carried out.

* * * * *